United States Patent [19]

Bedel et al.

[11] Patent Number: 5,539,005
[45] Date of Patent: Jul. 23, 1996

[54] POLYMERIC FOAMING AGENTS AND THEIR APPLICATION TO THE PREPARATION OF SYNTHETIC FOAMS

[75] Inventors: Didier Bedel, La Croix Saint Ouen; Chantal Crozat, Athies Sous Laon, both of France

[73] Assignee: Cray Valley, Verneuil en Halatte, France

[21] Appl. No.: 430,463

[22] Filed: Apr. 28, 1995

Related U.S. Application Data

[62] Division of Ser. No. 244,386, Sep. 29, 1994, Pat. No. 5,424,337.

[30] Foreign Application Priority Data

Dec. 12, 1991 [FR] France .................................. 91 15327

[51] Int. Cl.$^6$ ........................................................ C08J 9/10
[52] U.S. Cl. ............................................. 521/95; 521/128
[58] Field of Search ........................................ 521/95, 128

[56] References Cited

U.S. PATENT DOCUMENTS

| | | | |
|---|---|---|---|
| 2,754,599 | 9/1956 | Clifford et al. | 521/95 |
| 2,930,769 | 3/1960 | Haggis et al. | 521/95 |
| 4,772,640 | 9/1988 | Wolf et al. | 521/95 |

*Primary Examiner*—Morton Foelak
*Attorney, Agent, or Firm*—Finnegan, Henderson, Farabow, Garrett and Dunner

[57] ABSTRACT

Foamable composition comprising a mixture based on polymer resin and a effective quantity, in relation to the said resin, of blowing agent. The blowing agent comprises at least one $\alpha,\beta$-hydroxolated hydrocarbon azide.

Application to the production of articles made of synthetic foam.

18 Claims, No Drawings

POLYMERIC FOAMING AGENTS AND THEIR APPLICATION TO THE PREPARATION OF SYNTHETIC FOAMS

This is a division of application Ser. No. 08/244,386, filed Sep. 29, 1994, now U.S. Pat. No. 5,424,337.

The present invention relates to new foaming agents for polymers and to their application to the production of synthetic foams whose manufacture and/or use does not harm the ozone layer of the atmosphere.

Phenol-aldehyde foams, and more particularly phenol-formaldehyde foams, at present find increased utilisations in the building field and in the transportation industry because of their high thermal insulation and fire resistance. They are also employed in the form of blocks for domestic use, such as flower arrangement foams.

Other synthetic polymers find large-volume applications in the form of foams, such as, for example, polyurethanes, polystyrene, styrene-maleic anhydride copolymers, polyisoprene, polybutadiene, polyvinyl chloride, vinyl chloride-vinyl acetate, vinyl chloride-ethylene, vinyl chloride-vinylidiene [sic] chloride and vinyl chloride-acrylonitrile copolymers, polyethylene, polypropylene, tetrafluoroethylene-hexafluoropropylene copolymers, ethylene-vinyl acetate and ethylene-butyl acrylate copolymers, graft copolymers of vinyl chloride and alkyl acrylate, polyamides and polylactams.

These polymer foams, such as phenol-aldehyde foams, have in common the fact that their manufacture generally makes use, as blowing agent, of one or a number of completely halogenated hydrocarbons, especially chlorofluorocarbons known as CFCs. At the present time the use of chlorofluorocarbons (CFCs) presents serious ecological problems. In fact, these products are suspected of destroying the stratospheric ozone layer, and this can result in a greater penetration of solar UV rays and, consequently, considerable physiological disorders in living beings.

The CFCs are employed in particular for the manufacture of synthetic foams. Replacement of the CFCs by a less harmful gas represents a considerable ecological step forward. The solution most commonly adopted hitherto consists in replacing the CFCs with hydrochlorofluorocarbons (HCFCs). These products have been deliberately chosen for their greater instability, so as to be capable of decomposing before reaching the stratosphere. However, the environmental impact of these compounds remains so far unknown.

The problem which the present invention is intended to solve consists in providing a simple, economical and efficacious means for protecting the ozone layer of the atmosphere in the course of the manufacture and use of polymer foams. In the more particular context of phenol-aldehyde foams, a second problem which the present invention is intended to solve consists in developing a formulation capable of completely filling the mould employed in the course of this manufacture and capable of expanding during a short period while retaining the good thermal and acoustic insulation properties which are traditional in phenol-aldehyde foams.

These objectives are attained by virtue of the present invention by means of a foamable composition comprising a mixture based on polymer resin and an effective quantity, in relation to the said resin, of blowing agent, the said composition being characterised in that the blowing agent comprises at least one α,β-hydroxylated hydrocarbon azide. An α,β-hydroxylated hydrocarbon azide within the meaning of the present invention is intended to mean a compound of general formula

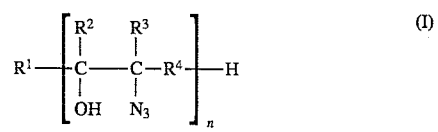

in which $R^1$, $R^2$ and $R^3$, which are identical or different, are chosen from the hydrogen atom and alkyl, aryl, aralkyl, alkylaryl and cycloalkyl radicals preferably containing up to 20 carbon atoms, $R^4$ is chosen from alkylene and arylene groups preferably containing up to 20 carbon atoms, and n is an integer approximately between 1 and 20.

The synthesis of such compounds has already been described in the literature, for example by addition of sodium azide to an oxirane of formula

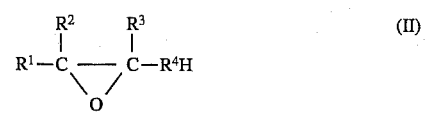

in which $R^1$ $R^2$ $R^3$ and $R^4$ have the meanings shown for the formula (I). Another known method of synthesis according to the literature consists in the addition of sodium azide to the compound of formula $C_6H_5$—CO—$CH_2Br$, followed by a reduction stage to obtain 2-azido-1-phenylethanol of formula $C_6H_5$—CHOH—$CH_2N_3$.

The following compounds may be mentioned as examples of α,β-hydroxylated hydrocarbon azides which can be employed in the present invention:

2-azidoethanol 2-azido-1-phenylethanol 1-azido-2-phenylethanol 1-chloro-3-azido-2-propanol 3-chloro-2-azidopropanol 1-azido-2-butanol 1,3-diazido-2-propanol 2-azidobutanol 3-phenoxy-2-azidopropanol 3-phenoxy-1-azido-2-propanol.

These compounds have the special property of a perfect solubility in resoles and polyols and, more generally, a high solubility in hydrophilic polymer resins. This special property gives them a considerable advantage, in addition to environmental acceptability, when compared with wholly or partially halogenated hydrocarbons such as chlorofluorocarbons (CFCs) and hydrogenated chlorofluorocarbons (HCFCs), which are maintained in emulsion in the hydrophilic resins generally by the additional presence of a surfactant in the foamable composition. In concrete terms, the solubility of the α,β-hydroxylated hydrocarbon azide in the polymer resin prevents it from being deposited during a prolonged storage of the foamable composition.

Under conditions which are generally utilised for foaming polymer resins, α,β-hydroxylated hydrocarbon azides are capable of rearranging, releasing nitrogen and forming a secondary amine of general formula:

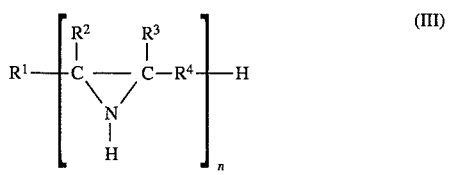

in which $R^1$, $R^2$, $R^3$ and $R^4$ have the meanings shown for formula (I). This secondary amine itself is capable of reacting with the polymer resin, especially when the latter is a phenolic resole or a polyurethane resin, and this has the effect of grafting the blowing agent onto the polymeric network and consequently preventing or at the very least considerably limiting the extraction of the blowing agent.

The polymer resin present in the composition according to the invention may be any thermoplastic or heat-curable polyaddition or polycondensation polymer capable of being expanded. It can be chosen in particular from polyurethanes, polystyrene, styrene-maleic anhydride copolymers, polyisoprene, polybutadiene, polyvinyl chloride, vinyl chloride-vinyl acetate, vinyl chloride-ethylene, vinyl chloride-vinylidiene [sic] chloride and vinyl chloride-acrylonitrile copolymers, polyethylene, polypropylene, tetrafluoroethylene-hexafluoropropylene copolymers, ethylene-vinyl acetate and ethylene-butyl acrylate copolymers, graft copolymers of vinyl chloride and alkyl acrylate, polyamides and polylactams and from phenol-aldehyde resins. The latter are well-known resins obtained preferably by condensation, in basic medium, of an aldehyde such as furfural or formaldehyde and of a phenol in an aldehyde/phenol molar ratio which is generally approximately between 0.8 and 1.5.

As indicated above, the composition according to the invention must include an effective quantity of the compound of formula (I), that is to say a quantity sufficient in relation to the polymer resin for the expansion of the said resin to take place within an industrially acceptable period of time. This effective quantity depends, of course, on the nature of the polymer resin to be expanded and its determination in each particular case is within the scope of a person skilled in the art, as a function of the essential requirements of the envisaged industrial process. It can be stated, nevertheless, that the compound of formula (I) is rarely efficient for expansion when employed in a proportion lower than 0.5 % by weight of the polymer resin. It will therefore be generally employed in a quantity of at least 0.5 % by weight of the resin. Furthermore, it is frequently noted that the ability of the resin to expand ceases to increase when the quantity of compound of formula (I) exceeds a certain level. Here again, this maximum quantity beyond which the effectiveness of the blowing agent according to the invention ceases to increase depends on the nature of the polymer resin and on the nature of the radicals $R^1$, $R^2$, $R^3$ and $R^4$, and its practical determination is within the scope of a person skilled in the art. It can be stated, nevertheless, that it is generally sufficient to employ the compound of formula (I) in a quantity not exceeding 15 % by weight of the polymer resin.

If appropriate, besides the polymer resin and the $\alpha,\beta$-hydroxylated hydrocarbon azide, the composition according to the invention may include other components, especially:

a conventional blowing agent such as an azo compound, a hydrazide, an azide, a nitroso compound, nitrourea, a carbonate or bicarbonate or a guanyl derivative, especially when its mixture with the $\alpha,\beta$-hydroxylated azide makes it possible to develop a specific synergism in the strength of expansion of the polymer resin or a specific property of the synthetic foam obtained. [sic]

a surface-active agent adapted to the polymer resin. Thus, in the case of phenol-aldehyde resins this may be polyalkylene glycol esters of unsaturated fatty acids, condensates of castor oil and alkylene oxide, castor oil itself or else one of its derivatives which are partially or completely hydrogenated and, if appropriate, alkoxylated, for example by means of ethylene, propylene or butylene oxides, nonylphenol ethoxylate, polysiloxane-polyethers copolymer and certain modified silicones. [sic]

a crosslinking catalyst, in the case of heat-curable polymer resins. In the case of phenol-aldehyde resins this may be an inorganic acid catalyst such as sulphuric acid, phosphoric acid and mixtures thereof, or else an organic acid catalyst such as benzenesulphonic acid, p-toluenesulphonic acid, xylenesulphonic acid, cumenesulphonic acid, phenolsulphonic acid and mixtures thereof in all proportions. Such acidic catalysts are generally employed in a proportion of approximately from 4 % to 25 % by weight of the phenol-aldehyde resin;

a catalyst for decomposition of the $\alpha,\beta$-hydroxylated hydrocarbon azide to an amine of formula (III). This may be especially a phosphine such as a triarylphosphine. Such a catalyst is generally employed in a proportion of approximately from 1% to 15 % by weight of the polymer resin; an inorganic compound such as especially a zeolite or glass fibres.

A second subject of the present invention consists of a process for the manufacture of synthetic foam, consisting in subjecting to foaming conditions a composition comprising a polymer resin and an effective quantity, in relation to the said resin, of at least one blowing agent, characterised in that the composition subjected to foaming is a composition as described above. The foaming conditions which can be employed in the process according to the invention differ, of course, depending on the particular $\alpha,\beta$-hydroxylated hydrocarbon agent chosen, on the one hand, and, on the other hand, on the nature of the polymer resin subjected to expansion. However, these conditions do not differ considerably from the expansion conditions used with traditional blowing agents for a given polymer resin. In most cases these conditions include temperature conditions which are milder than those usually utilised with traditional blowing agents. In the case of phenolic resoles, for example, the composition is raised to a temperature of approximately between 20° C. and 50° C. for a period—which is a function of the temperature—of approximately between 1 and 10 minutes. These time and temperature conditions enable the composition according to the invention to expand and crosslink while filling the whole of the mould and while providing articles made of phenol-aldehyde foam of good appearance, which have a satisfactory thermal insulation coefficient. The process according to the invention makes it possible to obtain without difficulty articles made of phenol-aldehyde foam of very different densities, commonly ranging approximately from 40 to 150 kg/m³. When reinforcements such as glass fibres are added to the composition, it is possible to obtain—depending on the proportion of these reinforcements in the composition—lightweight laminates with a density ranging approximately from 150 to 800 kg/m³.

A final subject of the present invention relates to finished products made of synthetic foam and obtained by making use of the process described above. These finished products find very varied applications depending on the nature of the starting polymer resin. In the case of phenol-aldehyde resins it is possible to mention sheets and panels of various forms intended for thermal insulation in the building, public works and transportation industries, for example for the strengthening of mine galleries and tunnels, as well as blocks for domestic use such as blocks of foam for flower arrangements. In the case of polyurethanes is it possible to mention foams which, because of their good compressive strength, can be employed in furniture as seat packings and in the motor vehicle industry. In the case of thermoplastic resins such as polyvinyl chloride, polystyrene, polyethylene and polypropylene, it is possible to mention foams employed as packing and packaging materials. The examples below are given by way of illustration and without limiting the present invention. Unless stated otherwise, all the quantities are expressed on a weight basis.

EXAMPLE 1 to 4

A solution of 0.83 mol of oxirane in 1300 ml of dioxane is heated to reflux. A solution of 1.15 mol of sodium azide in 175 ml of water is then added dropwise. The reaction mixture is kept under reflux for 20 hours. The organic phase is then recovered and the aqueous phase is extracted with 2 to 100 ml portions of dioxane. The organic phases are combined, dried over magnesium sulphate and the dioxane is removed by distillation under reduced pressure. The crude product thus obtained can be employed without further purification. The following are mixed so as to obtain a clear solution:

- 100 parts of a phenol-formaldehyde resin marketed by Cray Valley SA under reference Norsophen N1205,
- X parts of surfactant (condensate of ethylene oxide and castor oil) marketed by the Société Française d'Organosynthèse under the name Cemusol B,
- Y parts of catalyst marketed by Cray Valley SA under the name C 2965 and consisting of 27.8 % by weight of 65% paratoluenesulphonic acid, 64.8 % by weight of 70% phenolsulphonic acid, 3.7 % by weight of resorcinol and 3.7 % by weight of water,
- Z parts of a blowing agent prepared according to the method of synthesis described above. This blowing agent is azidophenylethanol (Example 1), azidochloropropanol (Example 2), azidobutanol (Example 3) or azidophenoxypropanol (Example 4).

The solution obtained is then poured into a mould at a temperature of 22° C. The expansion starts rapidly and reaches an expansion factor (ratio of the final volume to the initial volume) V shown in Table I below at the same time as the values of X, Y, and Z.

TABLE I

| Example | X | Y | Z | V |
|---|---|---|---|---|
| 1 | 4 | 13 | 5 | 8 |
| 2 | 4 | 13 | 2 | 10 |
| 3 | 3 | 13 | 5 | 12.5 |
| 4 | 3 | 15 | 5 | 8 |

EXAMPLE 5 to 7

5 parts of a blowing agent prepared according to the method of synthesis described in Examples 1–4 are dissolved in 50 parts of polyetherpolyol component of the polyurethane marketed by Weber S. A. under the name Marithan® EN. The blowing agent employed is azidophenoxypropanol (Example 5), azidophenylethanol (Example 6) or azidochloropropanol (Example 7). Furthermore, W parts of triphenylphosphine are dispersed in 50 parts of diphenylmethane diisocyanate. The two components are then mixed and the mixture is poured into a mould at a temperature of 22° C. Expansion starts rapidly and reaches an expansion factor (ratio of the final volume to the initial volume) V shown in, Table II below at the same time as the value of W.

| Example | 5 | 6 | 7 |
|---|---|---|---|
| W | 7 | 8 | 10 |
| V | 6 | 7 | 9 |

We claim:
1. A finished product made of synthetic foam obtained by subjecting to foaming conditions a foamable composition comprising a polymer resin and an effective quantity, in relation to the said resin, of a blowing agent which comprises at least one α,β-hydroxylated hydrocarbon azide.

2. Finished products according to claim 1, characterized in that the blowing agent comprises at least one compound of general formula

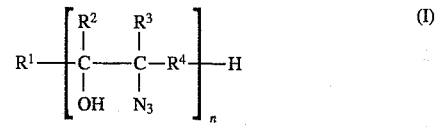

in which:

R$^1$, R$^2$ and R$^3$, which are identical or different, are chosen from hydrogen azide and alkyl, aryl, aralkyl, alkylaryl and cycloalkyl radicals preferably containing up to 20 carbon atoms;

R$^4$ is chosen from alkylene and arylene groups preferably containing up to 20 carbon atoms; and n is an integer between 1 and 20.

3. A finished product according to claim 1 wherein the blowing agent comprises at least one compound selected from 2-azido-1-phenylethanol, 1-azido-2-phenylethanol, 1-chloro-3-azido-2-propanol, 3-chloro-2-azidopropanol, 1-azido-2-butanol, 2-azidobutanol, 3-phenoxy-2-azidopropanol, or 3-phenoxy-1-azido-2-propanol.

4. A finished product according to claim 1 wherein the resin is selected from polyurethanes, polystyrene, styrene-maleic anhydride copolymers, polyisoprene, polybutadiene, polyvinyl chloride, vinyl chloride-vinyl acetate, vinyl chloride-ethylene, vinyl chloride-vinylidiene chloride and vinyl chloride-acrylonitrile copolymers, polyethylene, polypropylene, tetrafluoroethylene-hexafluoropropylene copolymers, ethylene-vinyl acetate, ethylene-butyl acrylate copolymers, graft copolymers of vinyl chloride and alkyl acrylate, polyamides, polyactams, or phenol-aldehyde resins.

5. A finished products according to claim 1 wherein the α,β-hydroxylated hydrocarbon azide is employed in a quantity of at least 0.5% of the weight of the polymer resin.

6. A finished product according to claim 1 wherein the α,β-hydroxylated hydrocarbon azide is employed in a quantity of not more than 15% by weight of the polymer resin.

7. A finished product according to claim 1 wherein the foamable composition additionally includes a blowing agent selected from azo compounds, hydrazides, azides, nitroso compounds, nitrourea, carbonates, bicarbonates, or guanyl derivatives.

8. A finished product according to claim 1 wherein the foamable composition additionally includes a surface-active agent.

9. A finished product according to claim 8, in which the polymer resin is a phenol-aldehyde resin and the surface-active agent is selected from polyalkylene glycol esters of unsaturated fatty acids, condensates of castor oil and alkylene oxide, castor oil itself or else one of its derivatives which are partially or completely hydrogenated and, if appropriate, alkoxylated, for example by means of ethylene, propylene or butylene oxides, nonylphenol ethoxylate, polysiloxane-polyether copolymers, and certain modified silicones.

10. A finished product according to claim 1 in which the polymer resin is heat-curable and includes a crosslinking catalyst.

11. A finished product according to claim 10, in which the polymer resin is a phenol-aldehyde resin and the crosslinking catalyst is an inorganic or organic acid.

12. A finished product according to claim 11 wherein said catalyst is employed in a proportion in the range of 4% to 25% of the weight of the phenol-aldehyde resin.

13. A finished product according to claim 2 wherein the foamable composition additionally includes a catalyst for decomposition of the α,β-hydroxylated hydrocarbon azide to an amine of formula III:

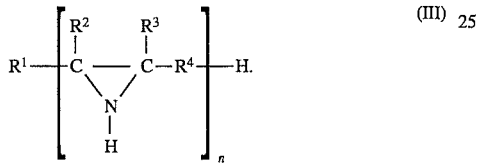

14. A finished product according to claim 13 wherein said decomposition catalyst is a phosphine.

15. A finished product according to claim 14 wherein said decomposition catalyst is employed in a proportion in the range of 1% to 15% by weight of the polymer resin.

16. A finished product according to claim 13 wherein said decomposition catalyst is employed in a proportion in the range of 1% to 15% by weight of the polymer resin.

17. A finished product according to claim 1 wherein the foamable composition additionally includes an inorganic compound selected from zeolites and glass fibers.

18. A finished product according to claim 1, wherein the blowing agent comprises at least one compound of the formula (I):

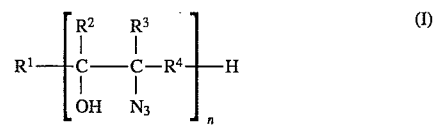

in which:

$R^1, R^2$, and $R^3$, which are identical or different, are chosen from hydrogen azide and alkyl, aryl, aralkyl, alkylaryl, and cycloalkyl radicals preferably containing up to 20 carbon atoms;

$R^4$ is chosen from alkylene and arylene groups preferably containing up to 20 carbon atoms; and n is an integer in the range of 1 to 20.

* * * * *